United States Patent [19]
Okada

[11] 4,105,784
[45] Aug. 8, 1978

[54] PLANT VIRAL DISEASE INHIBITOR

[75] Inventor: Fumio Okada, Shizuoka, Japan

[73] Assignee: Director of National Research Institute of Tea, Japan

[21] Appl. No.: 816,517

[22] Filed: Jul. 18, 1977

[30] Foreign Application Priority Data

Jul. 23, 1976 [JP] Japan .................................. 51-87248

[51] Int. Cl.$^2$ ........................ A01N 9/23; A01N 9/08; C07D 311/02
[52] U.S. Cl. ................................ 424/283; 260/345.2; 424/195; 47/DIG. 9; 47/DIG. 10; 47/DIG. 11
[58] Field of Search ............................. 424/195, 283; 260/345.2

[56] References Cited
PUBLICATIONS

Roberts et al., J. Sci. Food Agric. vol. 10, Mar. 1959, pp. 177–179.
Brown et al., Tetrahedron Letters No. 11, (1966) pp. 1193–1204.
Lyons, "Plant Names– Scientific & Popular", published by Nelson, Baker & Co., Detroit (1900), pp. 460 & 461.

*Primary Examiner*—Donald B. Moyer
*Attorney, Agent, or Firm*—Koda and Androlia

[57] ABSTRACT

A plant viral disease inhibitor containing as an active ingredient thereof at least one material selected from the group consisting of theaflavin and its derivatives represented by the general formula:

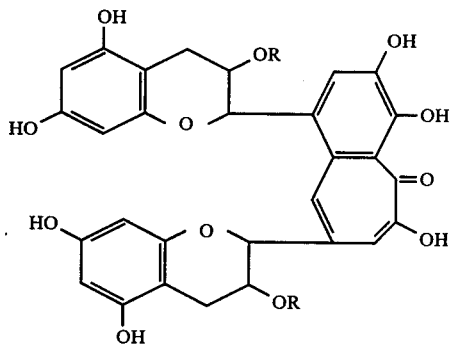

wherein R is hydrogen or

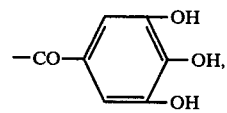

and their analogues.

7 Claims, 12 Drawing Figures

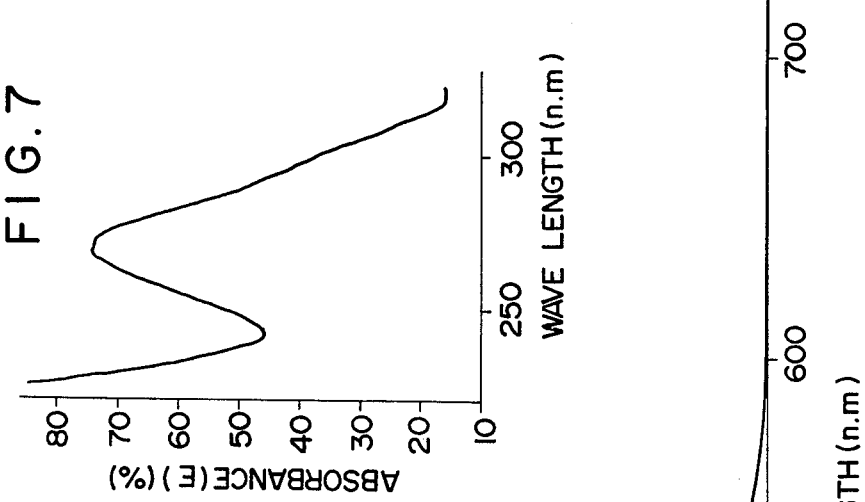
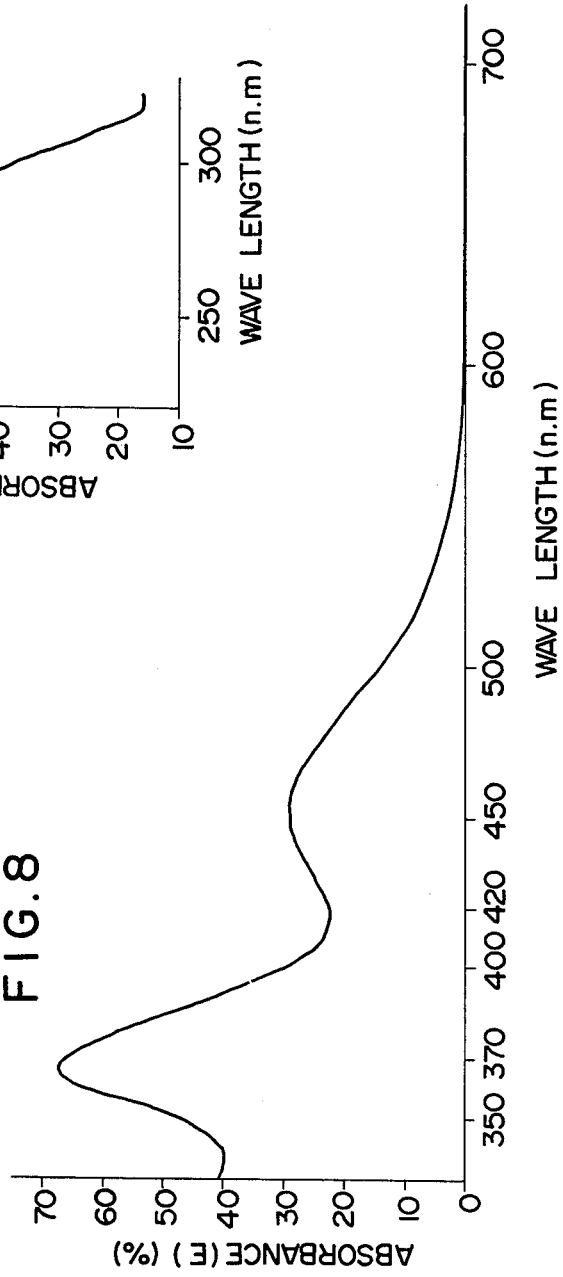
FIG. 7
FIG. 8

PLANT VIRAL DISEASE INHIBITOR

BACKGROUND OF THE INVENTION

1. Field of the Invention

The present invention relates to a plant viral disease inhibitor. More particularly, the present invention is concerned with plant viral disease inhibitor containing those components extracted from leaves of tea as active ingredient thereof.

2. Description of the Prior Art

Hitherto, research has been conducted in connection with the pharmacological action of tea. However, substantially no single component contained in tea has been experimented or tested to evidence the effect thereof.

The inventor has endeavored to find new uses for tea, in particular, to make the most of tea without wasting any part thereof as a pharmaceutically or biologically active agent, e.g. a biocide. During the investigations, it has been found that an extract of tea prevents generation of Dahlia mosaic virus, Crotalaria mosaic virus and Adzuki mosaic virus, and furthermore that the tannin of tea controls the diseases of a Japanese bladder cherry, an eggplant, a tomato, tobacco-By No. 4, etc., which have been inoculated with Tobacco mosaic virus. Thus, it has now been found that theaflavin contained in leaves of tea and its derivatives have an action to inhibit plant viral diseases.

SUMMARY OF THE INVENTION

The present invention provides a plant viral disease inhibitor which contains as an active ingredient thereof at least one material selected from the group consisting of theaflavin and its derivatives represented by the general formula:

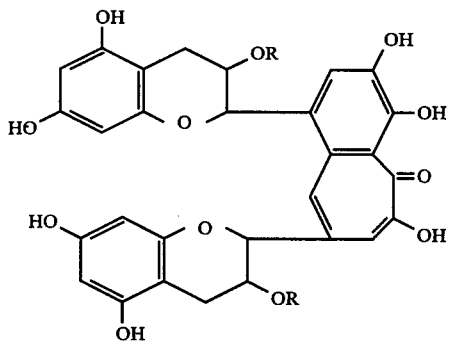

wherein R is hydrogen or

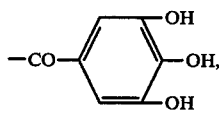

and their analogues.

BRIEF DESCRIPTION OF THE DRAWINGS

FIG. 7 is an ultraviolet zone absorption spectrum of TF-3;

FIG. 8 is a visible zone absorption spectrum of TF-3;

DETAILED DESCRIPTION OF THE INVENTION

Figure 1:
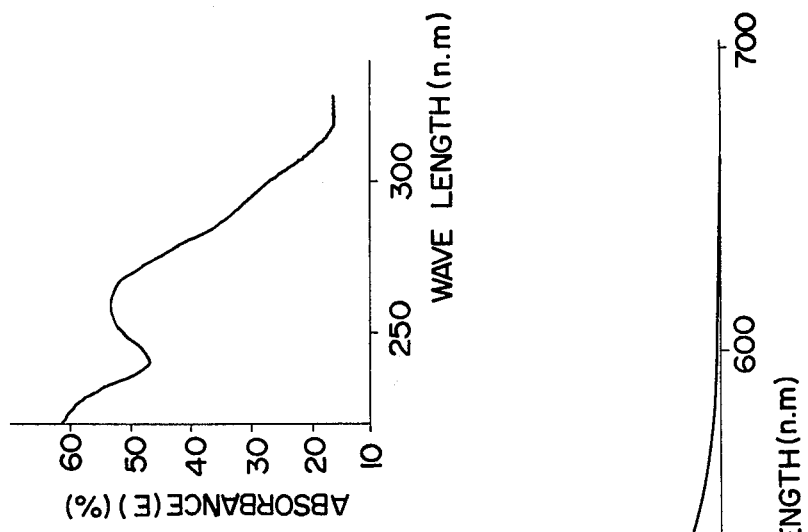
FIG. 1 is an ultraviolet zone absorption spectrum of TF-1.

The compounds represented by the above formula are theaflavin (both of R are hydrogen), theaflavin monogalate (one of R is

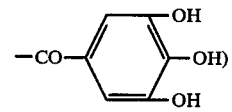

and theaflavin digalate (both of R are

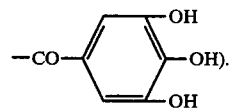

In addition to these compounds, the present invention includes their analogues obtained by purifying the above compounds.

Theaflavin, its derivatives and their analogues can be obtained from leaves of tea as a raw material.

For example, the leaves of tea fermented (including black tea) are extracted with water (including warm water and hot water) or an organic solvent to obtain phenolic dyes, or the catechin of green tea is treated with an oxidation enzyme and an oxidizing agent to obtain the phenolic dyes. After caffeine and the like are removed from these dyes, the remainder is dissolved in an organic solvent. The resulting organic solvent solution is subjected to partition by liquid chromatography using an acidic or neutral ion exchanger such as the Sephadex (a cross-linked dextran) and a nonionic exchanging fixed phase (e.g., octadecyl hydrocarbon, aliphatic acid esters, silicic acid material and the like) whereby theaflavin, theaflavin monogalate and theaflavin digalate can be obtained.

Furthermore, these fractions are again passed through a Sephadex LH-20 column and then dissolved in an organic solvent. After the organic solvent solution is concentrated and the organic solvent is distilled away, the fractions are dissolved in water. The resulting aqueous solution is subjected to partition by the use of a cellulose column whereby the analogues of theaflavin and its derivatives can be obtained. These analogues, if desired, are dissolved in an organic solvent and concentrated under reduced pressure. As an aqueous solution, it is flowed down an organic solvent layer and then separated into an aqueous layer and an organic solvent layer. On crystallization from the aqueous layer, purified analogues can be obtained.

Hereinafter, the above separation process will be explained in more detail as an embodiment of this invention.

One kilogram of black tea is extracted with five portions of hot water and the combined hot extract is allowed to cool down to room temperature. The extract so obtained is dissolved in isobutyl methyl ketone and the resulting isobutyl methyl ketone solution is concentrated to one liter under reduced pressure. This solution is washed with 2.5% $NaHCO_3$—$H_2O$ and alkalis contained therein are then removed by three or more times of water-washing. 300 ml of an aqueous solution containing the extract is prepared and treated with chloroform three times to remove caffeine contained therein.

The extract from which caffeine has been removed, is then dissolved in ethyl acetate and concentrated under reduced pressure whereby 20 grams of solids are obtained. These solids are dissolved in a mixed solution of 43% acetone and 57% water and introduced into a Sephadex LH-20 column. Partition of the solution is carried out using 43% acetone and 57% water whereby three fractions (F-1, F-2 and F-3) are obtained.

Each of these fractions is passed through again through the Sephadex LH-20 column using 40% acetone and 60% water. The acetone is distilled away under reduced pressure and the resulting precipitate is dissolved in ethyl acetate. The ethyl acetate solution is concentrated under reduced pressure and the ethyl acetate is distilled away. The precipitate is then dissolved in water and the resulting aqueous solution is charged to a cellulose column (200 to 300 mesh). Partition is carried out using water. Only water-soluble materials are combined together and dissolved in ethyl acetate (that is to say, the same procedure is repeated). The ethyl acetate solution is concentrated under reduced pressure and the ethyl acetate is distilled away. After being dissolved in water, the precipitate is flowed down through an ethyl acetate layer as an aqueous solution whereby a water layer and an ethyl acetate layer are formed.

The water layer is allowed to stand and the precipitate obtained is dissolved in n-butyl alcohol. The n-butyl alcohol solution is concentrated under reduced pressure to dryness. The residue is dissolved in water and allowed to stand whereupon the analogues corresponding to the above fractions (i.e. F-1→ TF-1; F-2 → TF-2; and F-3 → TF-3) are obtained.

As organic solvents which can be used in the above described separation method, ethyl acetate, methyl isobutyl ketone, n-butyl alcohol, acetone, chloroform and the like can be listed.

Figure 2:
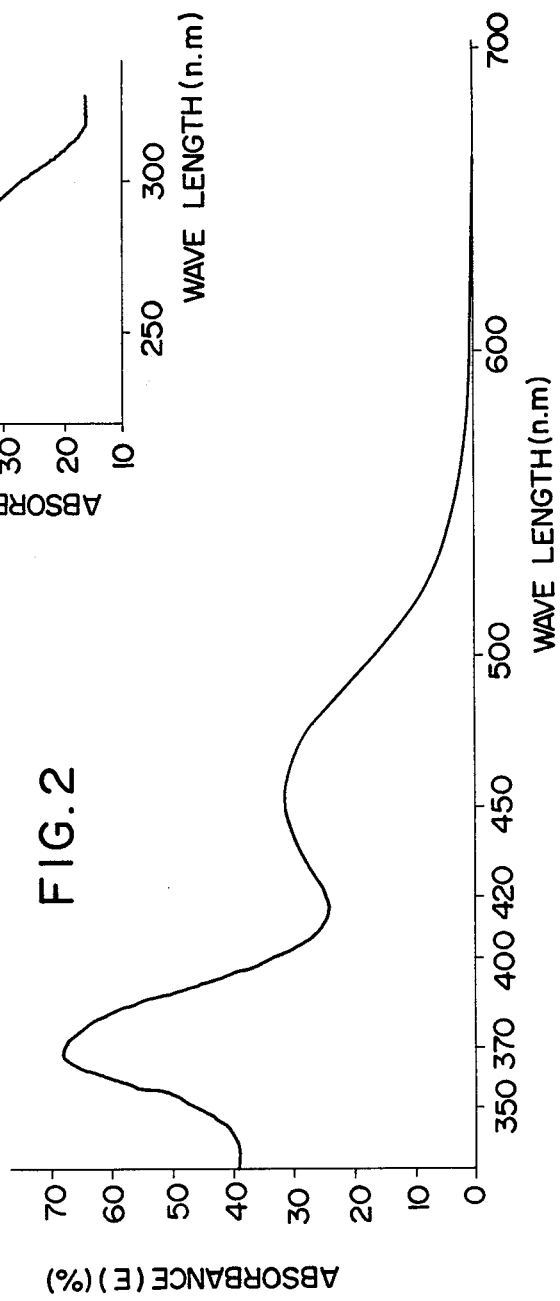
FIG. 2 is a visible zone absorption spectrum of TF-1.
Figure 3:
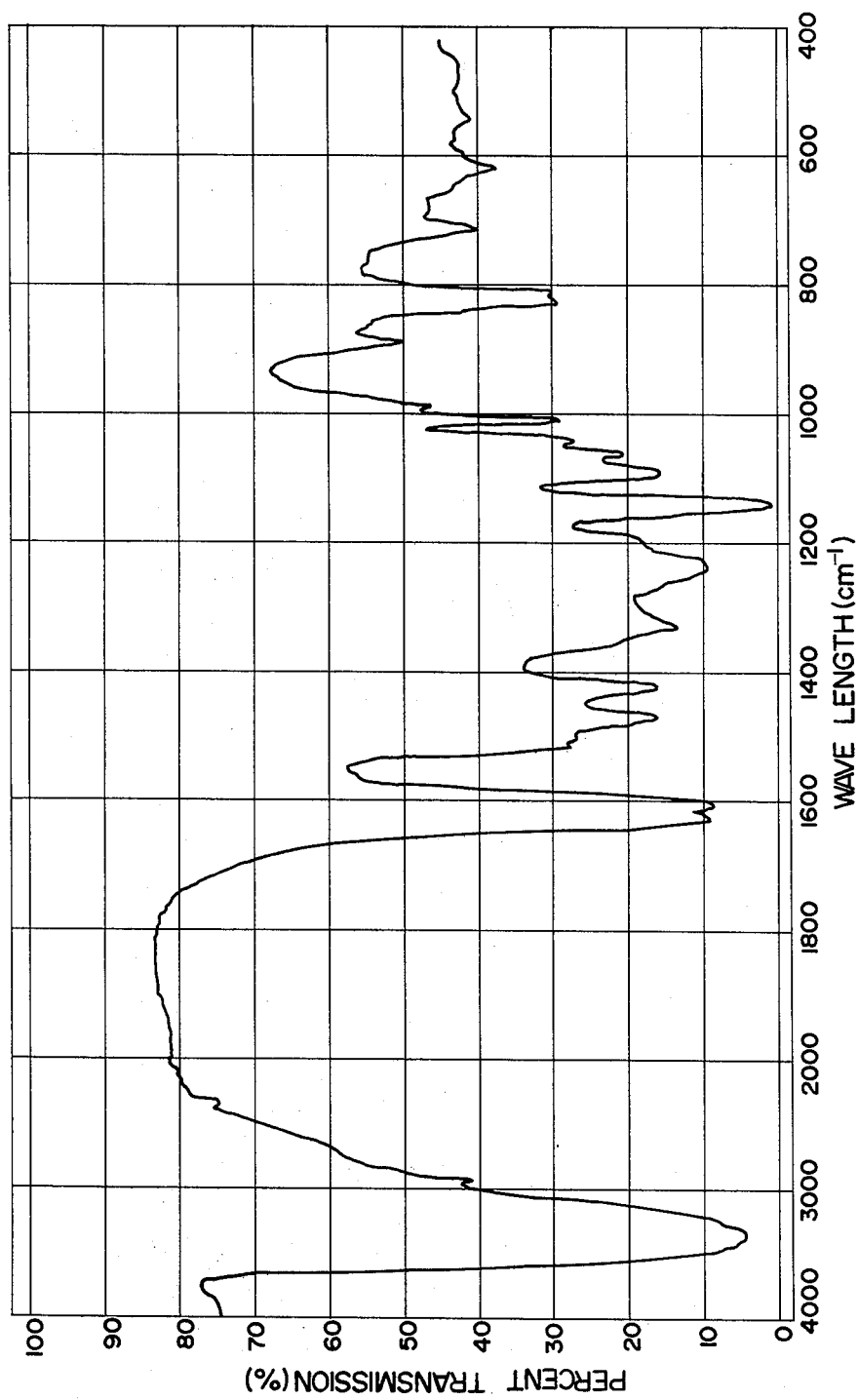
FIG. 3 is an infrared ray absorption spectrum of TF-1.
Figure 4:
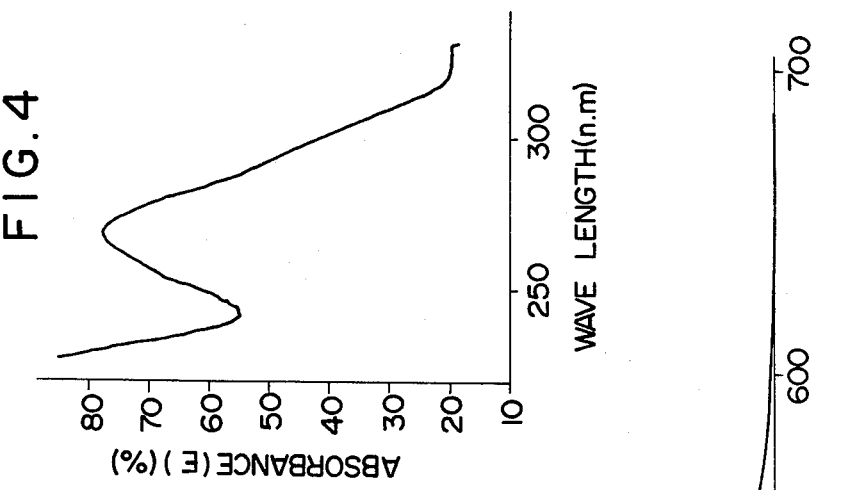
FIG. 4 is an ultraviolet zone absorption spectrum of TF-2.
Figure 5:
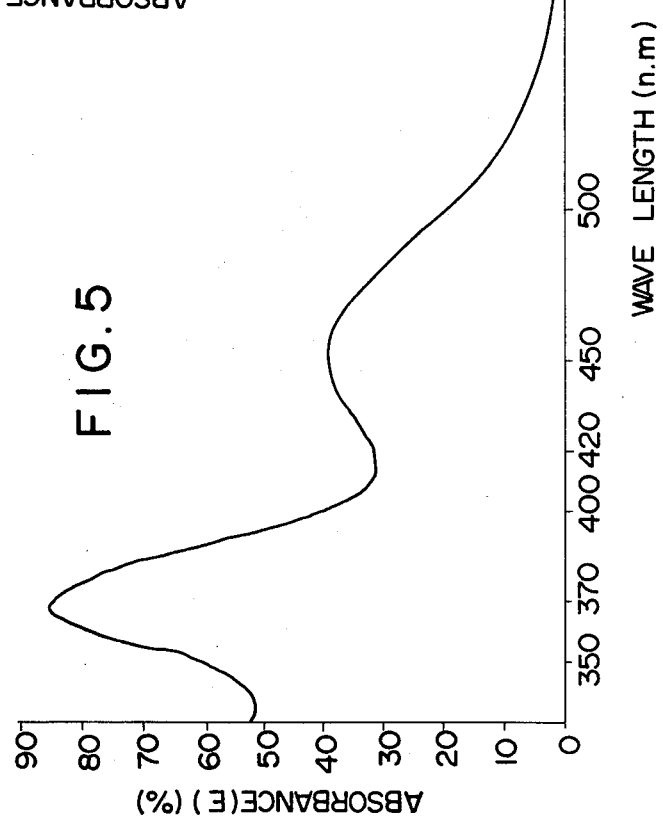
FIG. 5 is a visible zone absorption spectrum of TF-2.
Figure 6:
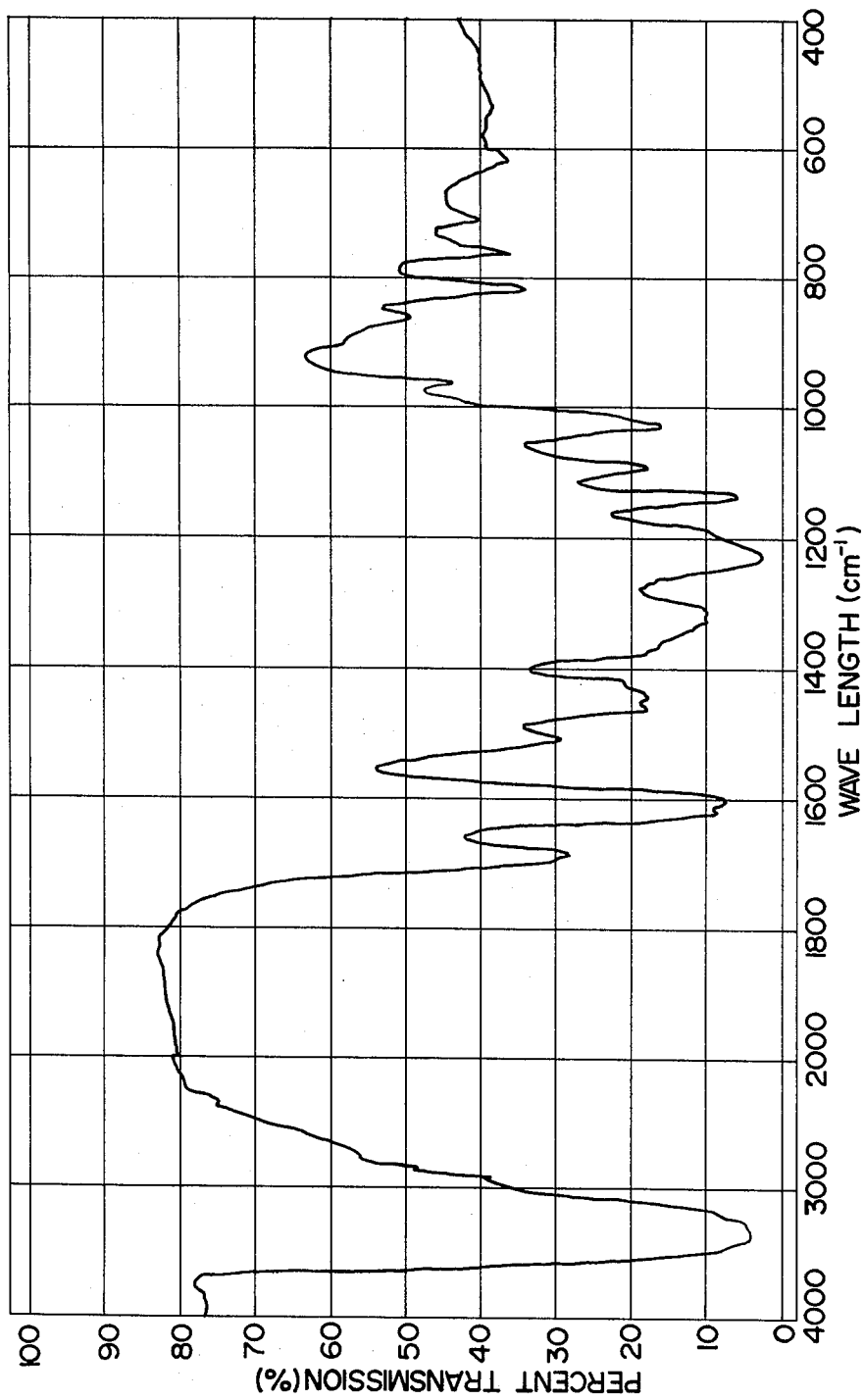
FIG. 6 is an infrared ray absorption spectrum of TF-2.
Figure 9:
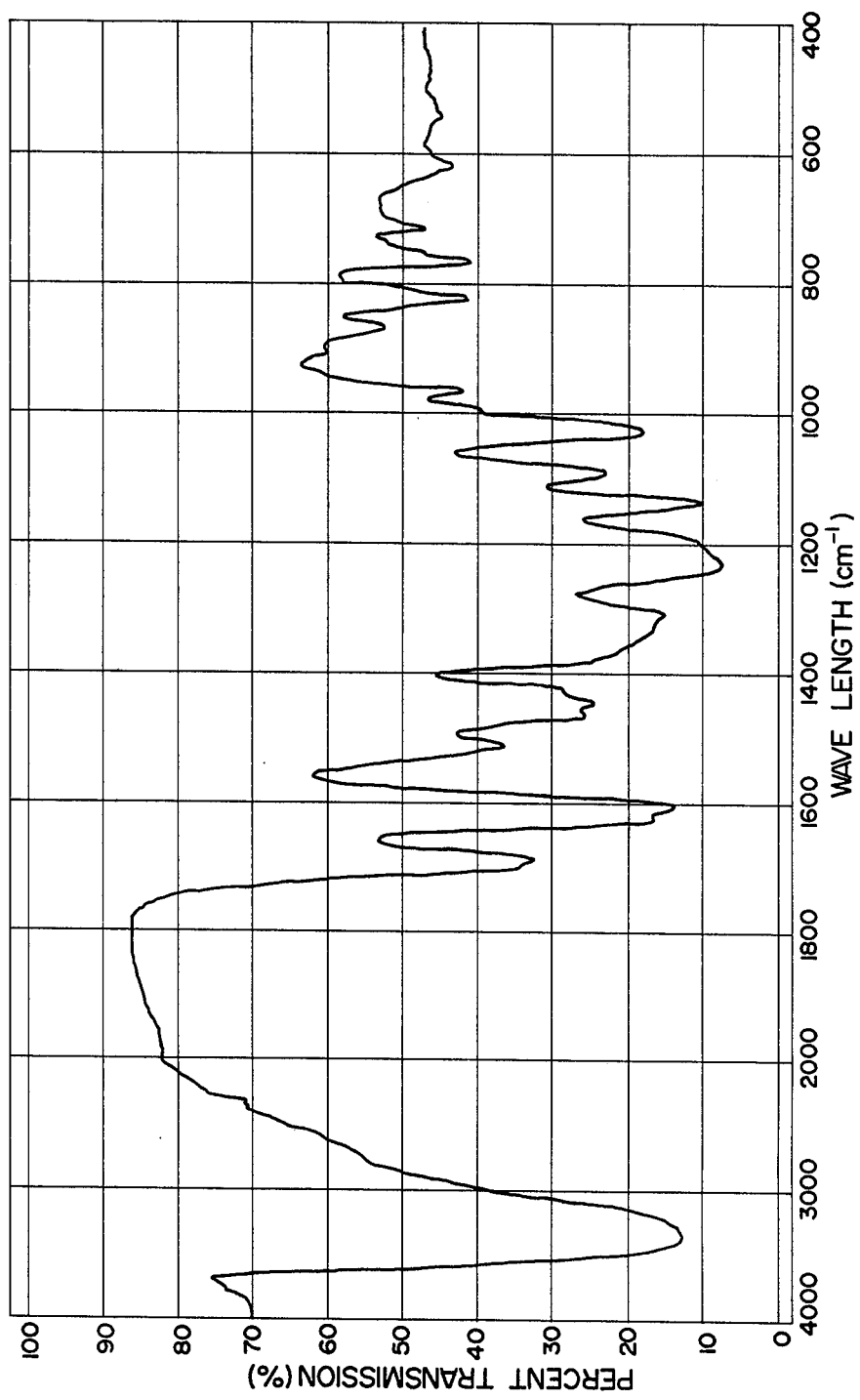
FIG. 9 is an infrared ray absorption spectrum of TF-3.
Figure 10:
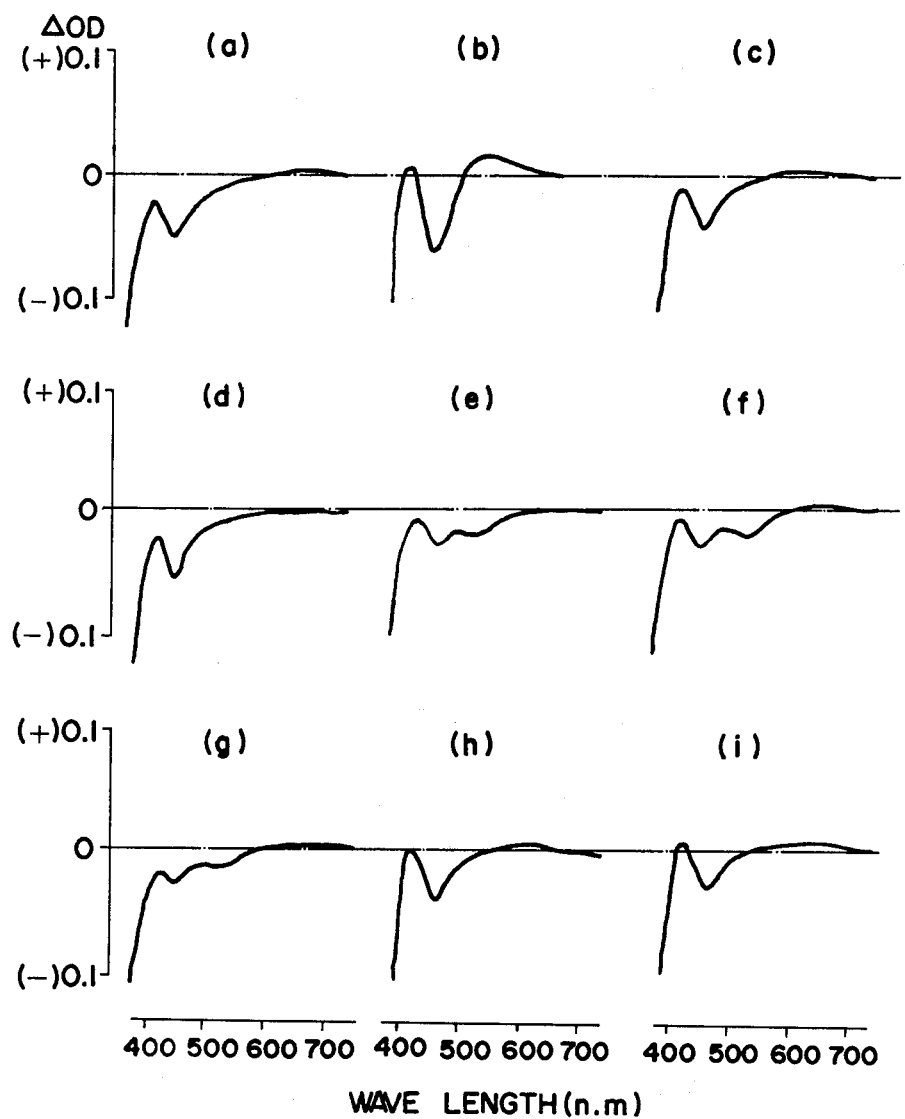
FIGS. 10(a) to (i) are curves showing a change in absorption of TF-2 by various nucleic acids and their derivatives.
Figure 11:
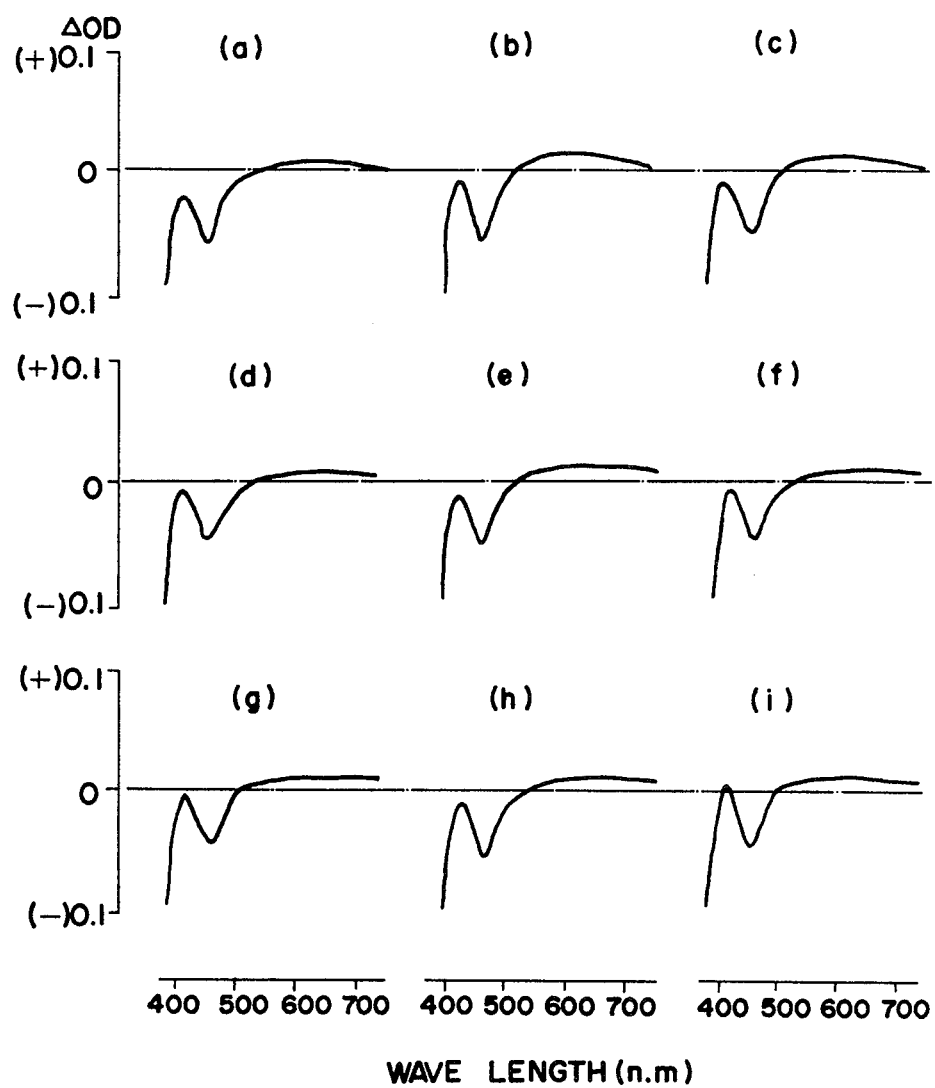
FIGS. 11(a) to (i) are curves showing a change in absorption of TF-3 by various nucleic acids and their derivatives.
Figure 12:
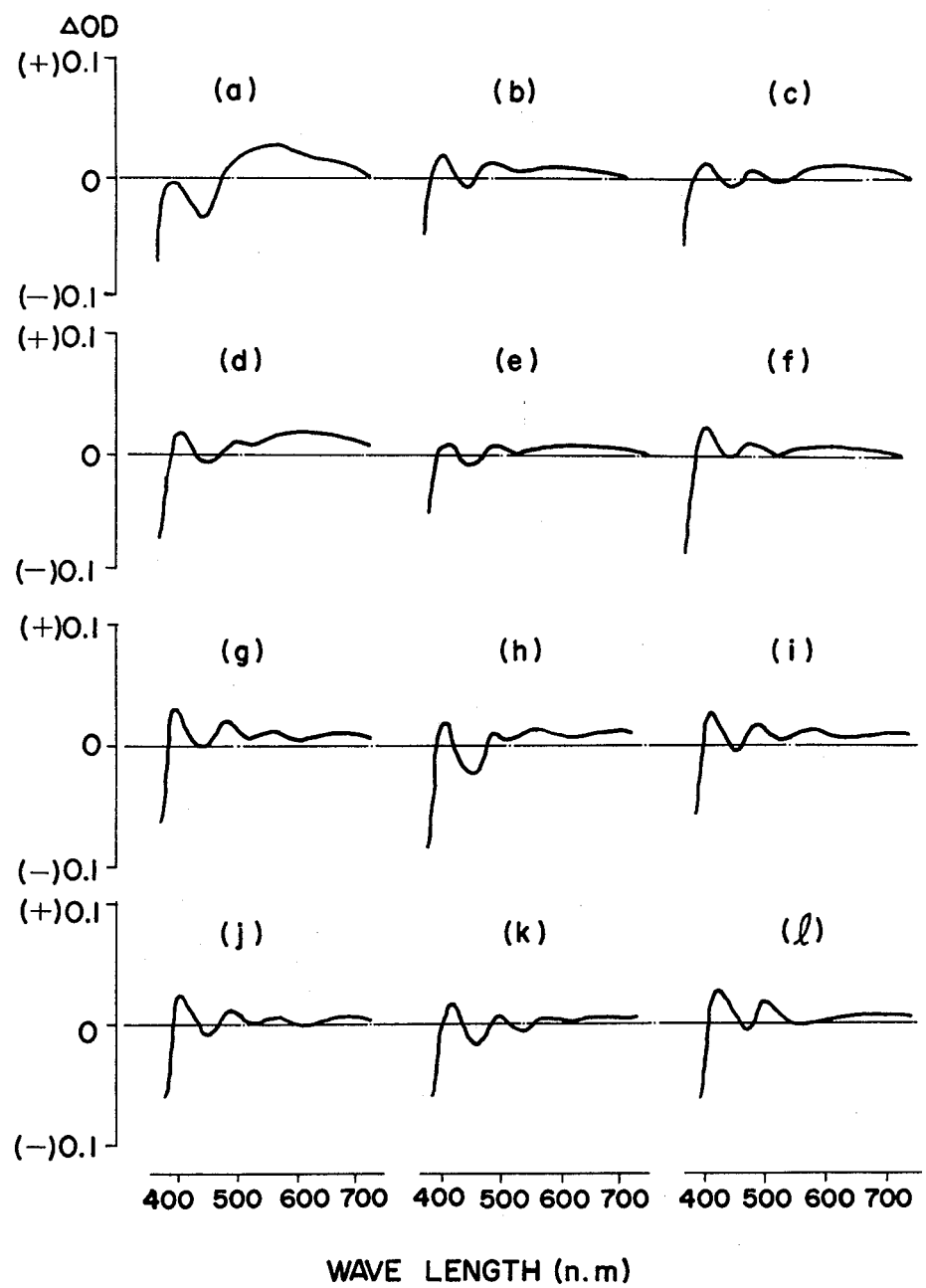
FIGS. 12(a) to (l) are curves showing a change in absorption of TF-2 and TF-3 by the components of nucleic acid.

FIG. 1 is an ultraviolet zone absorption spectrum of an analogue of theaflavin (hereinafter, referred to as "TF-1"), FIG. 2 is a visible zone absorption spectrum of TF-1, FIG. 3 is an infrared ray absorption spectrum of TF-1, FIG. 4 is an ultraviolet zone absorption spectrum of an analogue of theaflavin monogalate (hereinafter, referred to as "TF-2"), FIG. 5 is a visible zone absorption spectrum of TF-2, FIG. 6 is an infrared ray absorption spectrum of TF-2, FIG. 7 is an ultraviolet zone absorption spectrum of an analogue of theaflavin digalate (hereinafter, referred to as "TF-3"), FIG. 8 is a visible zone absorption spectrum of TF-3, and FIG. 9 is an infrared ray absorption spectrum of TF-3.

Elemental analytical values of TF-1, TF-2 and TF-3 are shown in Table 1.

Table 1

|  | Found | | Calculated | |
|---|---|---|---|---|
|  | C | H | C | H |
| Theaflavin Free Type | 55.29 | 4.86 | | |
| TF-1 | 54.82 | 4.50 | 61.70 | 4.29 |
| Theaflavin Monogalate | 53.49 | 4.57 | | |
| TF-2 | 57.20 | 4.24 | 60.34 | 3.94 |
| Theaflavin Digalate | 54.49 | 4.89 | | |
| TF-3 | 51.80 | 3.72 | 59.45 | 3.71 |

The theaflavin free type has a structural formula of $C_{29}H_{24}O_{12}$ and a molecular weight of 564.482; theaflavin monogalate, a structural formula of $C_{36}H_{28}O_{16}$ and a molecular weight of 716.584; and theaflavin digalate, a structural formula of $C_{43}H_{32}O_{20}$ and a molecular weight of 868,686.

The plant viral disease inhibitors of the present invention contain the above described active ingredients, singly or in admixture with each other.

Since these active ingredients are water-soluble, they are generally poured into soil as aqueous solutions thereof and absorbed in plants through their roots. As a matter of course, they can be absorbed in plants by other methods. Although the concentration of the active ingredients in the aqueous solutions is determined depending upon a plant to be administered, it is usually 0.1 to 100 milligrams per milliliter, preferably 0.3 to 45 milligrams per milliliter.

Viruses to which the inhibitors of the present invention can be effectively applied, are Tobacco mosaic virus (hereinafter, referred to as TMV), Cucumber mosaic virus (hereinafter, referred to as CMV), etc. It has been made clear that TMV lives upon those plants belonging to 198 species of 22 families, including tobacco, Solanacae, etc., and that CMV lives upon those plants belonging to 124 species of 45 families, including the gourd family and the aster family. Thus, viruses live upon a great number of plants.

Since the inhibitors of the present invention combine with either ribonucleic acid (RNA) or deoxyribonucleic acid (DNA), which play the leading part in infection and proliferation of these viruses, and furthermore, they act on the basic portions thereof, it can be expected that the inhibitors of the present invention will be effectively applied onto a number of viruses other than the above viruses.

Furthermore, the active ingredients of the present invention are natural compounds causing no damage from medicines and are the components of tea which is daily drunk. Taking into account the fact that not only a novel use of tea has been developed, but a product having no harm to human and animals has been produced, the practical value of the present invention is considered to be quite high.

The present invention will be explained in detail by reference to the following examples.

EXAMPLE 1

A 0.1 or 0.5% aqueous solution of a theaflavin mixture (mixture of theaflavin free type, theaflavin monogalate and theaflavin digalate) separated from black tea was prepared.

This aqueous solution was added to TMV inoculated pathogen and inoculated on leaves of tobacco. After a lapse of 2 days, the infection of TMV was examined comparing with a control area. The results obtained are shown in Table 2.

Table 2

| Run No. | Concentration | | | |
|---|---|---|---|---|
| | 0.1% | | 0.5% | |
| | Control Area | Inhibitor Added Area | Control Area | Inhibitor Added Area |
| 1 | 216 | 33 | 349 | 0 |
| 2 | 205 | 36 | 225 | 0 |
| Coefficiency of Inhibition | 83.6% | | 100% | |

The number of maculation was measured according to N. Glutinosa.

With the leaves of tobacco which was treated with the aqueous solution, no damages such as involution of the leaf edge and browning of leaf vein were detected.

EXAMPLE 2

In this example, each of a theaflavin free type, theaflavin monogalate and theaflavin digalate was examined with its capability to prevent infection of TMV. The active ingredients concentration of the aqueous solution was 0.5% and each capability was measured by the same method as used in Example 1. The results obtained are shown in Table 3.

Table 3

| Run No. | Theaflavin Free Type | | Theaflavin Monogalate | | Theaflavin Digalate | |
|---|---|---|---|---|---|---|
| | Control Area | Inhibitor Added Area | Control Area | Inhibitor Added Area | Control Area | Inhibitor Added Area |
| 1 | 224 | 56 | 301 | 0 | 513 | 0 |
| 2 | 416 | 80 | 360 | 0 | 405 | 0 |
| Coefficiency of Inhibition | 88.8% | | 100% | | 100% | |

The number of maculation was measured according to N. Glutinosa.

In this case, no damages on the leaves of tobacco which had been treated with the inhibitor were detected.

EXAMPLE 3

In this example, the inhibition effect of TF-3 on TMV-RNA virus activity was examined. The concentration oF TF-3 in the aqueous solution was $3 \times 10^{-4}$ mole. The aqueous solution was maintained at pH of 7.0 by using 0.1 mole of a phosphoric acid buffer or 0.01 mole of a sodium chloride solution. TMV-RNA having a concentration of 2 μg/ml was used. The results obtained are shown in FIGS. 4 and 5.

Table 4

| Test Date | Time for acting with Nucleic Acid | Area | Number of Maculation | | | | | Total | Coefficiency of Inhibition |
|---|---|---|---|---|---|---|---|---|---|
| | | | 1 | 2 | 3 | 4 | 5 | | |
| Dec. 19, '75 to Dec. 22, '75 | 0 hr | R | 510 | 404 | 385 | 506 | 466 | 2271 | 60.5% |
| | | S | 147 | 207 | 132 | 235 | 177 | 898 | |
| | 24 hrs | R | 261 | 454 | 155 | 344 | 122 | 1336 | 100.0% |
| | | S | 0 | 0 | 0 | 0 | 0 | 0 | |
| Jan. 7, '76 to Jan. 10, '76 | 0 hr | R | 708 | 449 | 293 | — | — | 1450 | 24.0% |
| | | S | 501 | 373 | 228 | — | — | 1102 | |
| | 24 hrs | R | 251 | 149 | 142 | — | — | 542 | 100.0% |
| | | S | 0 | 0 | 0 | — | — | 0 | |

R: Control Area
S: Inhibitor Added Area

Table 5

| Test Date | Time for acting with Nucleic Acid | Area | Number of Maculation | | | Total | Coefficiency of Inhibition |
|---|---|---|---|---|---|---|---|
| | | | 1 | 2 | 3 | | |
| Dec. 26, '75 to Dec. 28, '75 | 0 hr | R | 199 | 271 | 212 | 682 | 37.7% |
| | | S | 158 | 115 | 152 | 425 | |
| | 2 hrs | R | 521 | 182 | 740 | 1443 | 100.0% |
| | | S | 0 | 0 | 0 | 0 | |
| | 4 hrs | R | 217 | 624 | 259 | 1100 | 100.0% |
| | | S | 0 | 0 | 0 | 0 | |
| Jan. 6, '76 to Jan. 8, '76 | 0 hr | R | 423 | 257 | 233 | 913 | 75.6% |
| | | S | 107 | 72 | 44 | 233 | |
| | 2 hrs | S | 0 | 0 | 0 | 0 | 100.0% |
| | | R | 122 | 650 | 346 | 1118 | |
| | 4 hrs | S | 0 | 0 | 0 | 0 | 100.0% |

R: Control Area
S: Inhibitor Added Area

EXAMPLE 4

In order to examine the inhibition effect of TF-2 on TMV-RNA virus activity, the procedure of Example 3 was repeated with the exception that TF-2 was used in place of TF-3 and the concentration was $2.6 \times 10^{-4}$ mole. The results obtained are shown in Tables 6 and 7.

Table 6

| Test Date | Time for acting with Nucleic Acid | Area | Number of Maculation | | | | | Total | Coefficiency of Inhibition |
|---|---|---|---|---|---|---|---|---|---|
| | | | 1 | 2 | 3 | 4 | 5 | | |
| Dec. 19, '75 to Dec. 22, '75 | 0 hr | R | 252 | 306 | 317 | 381 | 408 | 1664 | 82.7% |
| | | S | 60 | 43 | 49 | 91 | 45 | 288 | |
| | 24 hrs | R | 218 | 572 | 247 | 249 | 195 | 1481 | 100.0% |
| | | S | 0 | 0 | 0 | 0 | 0 | 0 | |
| | 0 hr | R | 278 | 304 | 565 | — | — | 1147 | 25.7% |

Table 6-continued

| Test Date | Time for acting with Nucleic Acid | Area | Number of Maculation | | | | | Total | Coefficiency of Inhibition |
|---|---|---|---|---|---|---|---|---|---|
| | | | 1 | 2 | 3 | 4 | 5 | | |
| Jan. 7, '76 to Jan. 10, '76 | 24 hrs | S | 187 | 280 | 386 | — | — | 853 | |
| | | R | 218 | 310 | 356 | — | — | 884 | 100.0% |
| | | S | 0 | 0 | 0 | — | — | 0 | |

R: Control Area
S: Inhibitor Added Area

Table 7

| Test Date | Time for acting with Nucleic acid | Area | Number of Maculation | | | Total | Coefficiency of Inhibition |
|---|---|---|---|---|---|---|---|
| | | | 1 | 2 | 3 | | |
| Dec. 26, '75 to Dec. 28, '75 | 0 hr | R | 159 | 666 | 761 | 1586 | 97.1% |
| | | S | 6 | 29 | 11 | 46 | |
| | 2 hrs | R | 443 | 296 | 469 | 1208 | 100.0% |
| | | S | 0 | 0 | 0 | 0 | |
| | 4 hrs | R | 289 | 445 | 304 | 1038 | 100.0% |
| | | S | 0 | 0 | 0 | 0 | |
| Jan. 6, '76 to Jan. 8, '76 | 0 hr | R | 459 | 568 | — | 1027 | 70.1% |
| | | S | 128 | 180 | — | 308 | |
| | 2 hrs | R | 465 | 263 | — | 728 | 100.0% |
| | | S | 0 | 0 | — | 0 | |
| | 4 hrs | R | 544 | 573 | — | 1117 | 100.0% |
| | | S | 0 | 0 | — | 0 | |

R: Control Area
S: Inhibitor Added Area

EXAMPLE 5

In this example, a change in absorption of TF-2 by various nucleic acids and their derivatives was measured in order to examine the action of TF-2 on various viruses. This measurement was conducted under the conditions that the final concentration of TF-2 to 0.5 mg/ml and nucleic acid and its derivative be $1 \times 10^{-3}$ mole as phosphorus (0.01 mole acetic acid buffer solution, 0.01 mole NaCl, pH 5.5).

The results obtained are shown in FIG. 10(a) to (i) in which (a) to (i) indicate a change in absorption by DNA (double or single strandness), DNA (thermal modification), Apurinic-DNA, Apyrimidinic-DNA, Poly-U, Poly-C, Poly-A, Ehrlich ascites carcinoma-RNA and Escherichia coli- RNA, respectively.

EXAMPLE 6

In order to measure a change in absorption of TF-3 by various nuleic acids and their derivatives, the procedure of Example 5 was repeated with the exception that TF-3 was used in place of TF-2. In this case, the final concentration of the nucleic acids and their derivatives was $1 \times 10^{-4}$ mole as phosphorus. The results obtained are shown in FIG. 11(a) to (i), in which (a) to (i) indicate a change in absorption by DNA (double or single strandness), DNA (thermal modification), Apurinic-DNA, Apyrimidinic-DNA, Poly-U, Poly-C, Poly-A, Ehrlich ascites carcinoma-RNA and Escherichia coli-RNA, respectively.

EXAMPLE 7

In this example, a change in absorption of TF-2 and TF-3 by the components of nucleic acid was measured. In this case, the final concentration of TF-2 and TF-3 was 0.5 mg/ml and that of the component of nucleic acid was $1 \times 10^{-3}$ mole (0.01 mole acetic acid buffer solution, 0.01 mole NaCl, pH 5.5). The results obtained are shown in FIG. 12(a) to (l), in which (a) and (g), (b) and (h), (c) and (i), (d) and (j), (e) and (k), and (f) an (l) indicate a change in absorption by uracil, uridine, 5'-UMP, adenine, nucleoside, and 5'-AMP, respectively.

As apparent from Example 5 to 7, the active ingredients of the present invention combine with either DNA or RNA without discrimination, and furthermore they act together with any of their derivatives. It is also apparent that since they show combination action with Ehrlich ascites carcinoma-RNA and Escherichia coli-RNA, the action of these compounds is exerted on a quite large range in addition to plants. Furthermore, since these materials act with any of bases, nucleoside and nucleotide constituting nucleic acid, it is apparent that they combine directly with nucleic acid constituting bases. Also, it is shown that they have the same combination action as for any of pyrimidine and purine types.

What is claimed is:

1. A method for inhibiting viral diseases in plants comprising the steps of applying a plant viral disease inhibitor thereto, said inhibitor comprising a substance selected from the group consisting of theoflavin and its derivatives represented by the general formula:

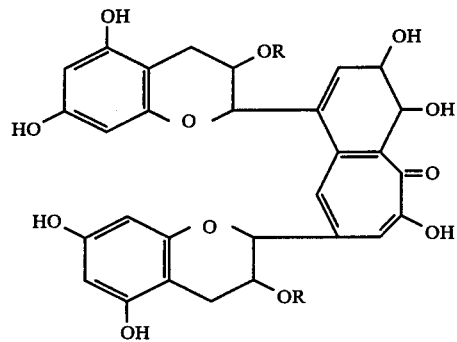

wherein R is hydrogen or

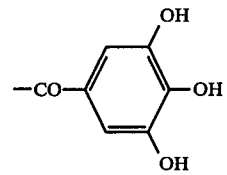

2. The method of claim 1 wherein said inhibitor comprises theaflavin.

3. The method of claim 1 wherein said inhibitor comprises theaflavin monogalate.

4. The method of claim 1 wherein said inhibitor comprises theaflavin digalate.

5. The method of claim 1 wherein said inhibitor is applied to said plant by pouring a solution of said inhibitor to the soil containing said plant, said solution comprising from about 0.1 to 100 milligrams per milliliter of solution.

6. The method of claim 1 wherein said inhibitor is a mixture of theaflavin, theaflavin monogalate and theaflavin digalate.

7. A method for inhibiting viral diseases in plants comprising the steps of applying a plant viral disease inhibitor thereto, said inhibitor comprising a mixture of at least two substances selected from the group consisting of theoflavin and its derivatives represented by the general formula:

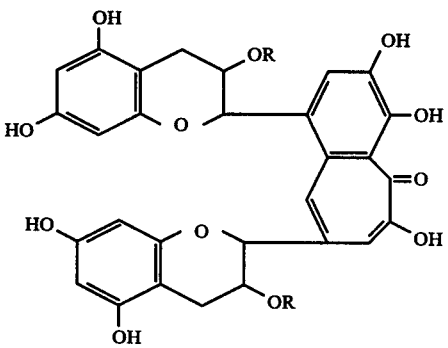

wherein R is hydrogen or

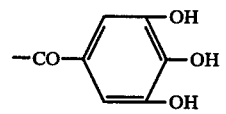

* * * * *